United States Patent [19]
Wolfbeis

[11] Patent Number: 5,238,809
[45] Date of Patent: Aug. 24, 1993

[54] METHOD FOR OPTICAL DETERMINATION OF THE CATALYTIC ENZYME ACTIVITY AND ARRANGEMENT FOR IMPLEMENTING THIS METHOD

[75] Inventor: Otto S. Wolfbeis, Graz, Austria

[73] Assignee: AVL Medical Instruments AG, Schaffhausen, Switzerland

[21] Appl. No.: 711,270

[22] Filed: Jun. 4, 1991

Related U.S. Application Data

[63] Continuation of Ser. No. 8,947, Jan. 30, 1987, abandoned.

[30] Foreign Application Priority Data

Feb. 3, 1986 [AT] Austria .................. 255/86

[51] Int. Cl.$^5$ .......................... C12Q 1/00; C12M 1/00; C12M 1/34
[52] U.S. Cl. .......................... 435/4; 435/287; 435/291; 435/310; 435/805; 435/808; 436/163; 436/164; 422/55; 422/56; 422/57; 422/58; 422/82.05; 422/82.06; 422/82.07

[58] Field of Search .................. 358/901; 435/4, 288, 435/310, 808, 805, 287; 436/163, 164; 422/55, 56, 57, 58, 60, 68, 82.05, 82.06, 82.07

[56] References Cited

U.S. PATENT DOCUMENTS

| | | | |
|---|---|---|---|
| 4,399,099 | 8/1983 | Buckles | 422/58 |
| 4,803,049 | 2/1989 | Hirschfeld et al. | 422/58 |

*Primary Examiner*—Esther L. Kepplinger
*Assistant Examiner*—Toni R. Scheiner
*Attorney, Agent, or Firm*—Watson, Cole, Grindle & Watson

[57] ABSTRACT

For optical determination of the catalytic enzyme activity of a sample by means of enzyme reactants which are split under the influence of the enzyme to be measured, the enzyme reactant is placed at the end of an optical fiber and brought into contact with the sample to be determined. The measurements are carried out by observing the rate of change in spectral characteristics of the enzyme reactant, or its reaction products, resulting from the enzyme reaction. The method permits measurements of undiluted blood and in-vivo determinations of enzyme activities.

16 Claims, 2 Drawing Sheets

METHOD FOR OPTICAL DETERMINATION OF THE CATALYTIC ENZYME ACTIVITY AND ARRANGEMENT FOR IMPLEMENTING THIS METHOD

BACKGROUND OF THE INVENTION

This application is a continuation of of application Ser. No. 008 947, filed Jan. 30, 1987, now abandoned.

This invention relates to a method of optically determining the catalytic enzyme activity of a sample, and a set-up for implementation of this method, the sample to be tested being in contact with an enzyme substrate or reactant.

Measuring the catalytic activity of enzymes is of great importance in biochemical and clinical analysis. Deviations from the normal activity often are typical of certain diseases. With bone or prostate tumors, for example, the activity of the "acid phosphatase" enzyme is markedly increased, and its determination will be most valuable from the point of view of diagnosis.

DESCRIPTION OF THE PRIOR ART

A number of methods have been developed in order to determine enzyme activities. They are summarized in the books by G. G. GUILBAULT: Enzymatic Methods of Analysis, Pergamon Press, Oxford, 1970; and by H. BERGMEYER: Grundlagen der enzymatischen Analyse, Verlag Chemie, Weinheim New York, 1977. Besides, identification of pathogenic bacteria by means of synthetic protease reactants has recently attracted interest (cf. COBURN, LYTLE and HUBER, in Anal. Chem. 57, 1669, 1985).

Conventionally the activity of enzymes is measured by means of coloured or fluorescent reactants which may be synthetic. For this purpose enzyme reactants are used which will decompose under the influence of the enzymes to form coloured products. The increase in colour or fluorescence intensity over time is used as a measure of enzyme activity. Hydrolases which are particularly well suited for testing by means of this kinetic method include carboxylesterases, phosphatases, sulphatases, dealkylases, glycosidases and proteases.

As a typical example a method of phosphatase measurement is cited in this context, which was designed by KOLLER and WOLFBEIS and is published in Analytical Biochemistry, 143, 146 (1984). In this method a phosphoric acid ester of structure A as below.

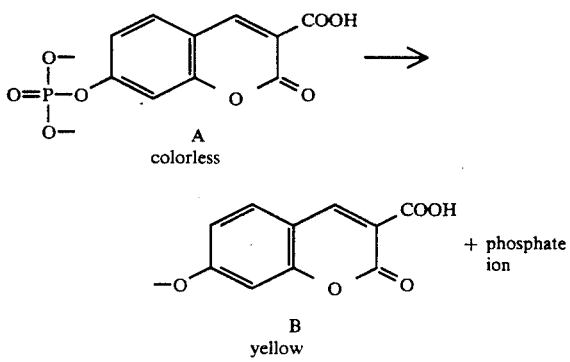

is split into two fragments by the "acid phosphatase" enzyme, to form a ionic product of hydrolysis B and a free phosphate ion. Contrary to the initial reactant A, the phenolate ion B is characterized by a vivid yellow colour and blue-green fluorescence. The increase in colour and fluorescence over time may be used as a direct measure of the activity of the acid phosphatase.

This method of determination is very sensitive and permits photometric determination of about 0.001 activity units of phosphatase per millilitre of the sample, and of about 60 microunits per millilitre with the fluorometric method.

Comparable methods are used for measuring carboxyl esterases, sulphatases and amylases.

As described in the above paper by COBURN, LYTLE and HUBER, it is also possible to measure proteases in this way, with the use of synthetic peptides or amides.

A feature common to all of these methods is the formation of a multi-coloured or fluorescent product as a consequence of enzyme reaction.

So far, enzyme activities have only been determined in vitro, as none of the known methods is suitable for application in the living organism. This would be desirable for various reasons, however, since in-vivo measurements may be performed faster and in real time, for instance. Contrary to this, the conventional methods employed up to now necessitate the taking of a sample, and cannot prevent errors which may occur in sampling and preparation work.

Besides, the above methods and all other methods of determination by means of synthetic enzyme reactants are only practicable if the solutions or samples are optically transparent. They cannot be used with undiluted blood and in-vivo tests.

SUMMARY OF THE INVENTION

It is an object of the present invention to present a method and corresponding set-up suitable for determining catalytic enzyme activities which will not have the above drawbacks and will permit in-vivo determinations of enzyme activities.

According to the invention this is achieved by placing an enzyme reactant at the end of an optical fiber and bringing it into contact with the sample to be tested, and by registering the rate of change in spectral properties of the enzyme reactant or its reaction products resulting from the enzyme reaction, and by using it for determination of the enzyme activity. In the present invention the problem of in-vivo testing is solved by placing an enzyme reactant, for example for hydrolytically active enzymes, at the end of an optical fiber. This end is brought into contact with the sample, the spectral properties of the reactant changing with the enzyme activity of the sample. The change is monitored via the optical fiber and is used as a measure of the prevalent enzyme activity. This method will permit for the first time the determination of enzyme activities even in undiluted blood and in other non-transparent liquids without the need for preparing a sample prior to testing.

In a further development of the method the proposal is put forward that the change in absorption of the—preferably synthetic—reactant, which is due to the enzymatic reaction, be observed via the optical fiber and used for determination of the enzyme activity.

According to another variant of the invention the spectral change in the fluorescence radiation of the—preferably synthetic—reactant, which is due to the enzymatic reaction, for example the change in fluorescence intensity or the shifting of the maximum of fluorescence, is observed via the optical fiber and used for measuring the enzyme activity. In one method, the excitation light scattered back by the reactant or its reaction products is measured, whose intensity will depend on the absorption capacity of the reactant which is influenced by the catalytic activity of the enzyme. In another method the change in the fluorescence intensity of the enzyme reactant due to the catalytic activity of the enzyme is measured via the optical fiber, for instance by means of a filter or an energy-dispersing detector system, and the values obtained are further evaluated.

Another variant of the invention provides that in addition to the activity of the enzyme, the pH-value of the sample be determined in a conventional manner, and that this value be used for correcting the value of the enzyme activity previously determined.

As is known, the velocity of many enzyme reactions will strongly depend on the pH-value of the solution. Besides, the degree of dissociation of many dyes released upon hydrolysis is pH-dependent. As the pH-value of physiological samples may vary within a certain range, it will be necessary to correct the actually obtained value for enzyme activity with regard to the pH. This is best done empirically. Although the pH-dependence of enzyme activity is known for a great number of enzymes, it must be newly determined in the instance of an immobilized enzyme reactant. For determination of the individual pH-value of the sample it will therefore be useful to measure the pH-value at the same time as the enzyme activity is determined. The true enzyme activity is best determined by using an empirically found relation between activity and relative signal change as a function of the actual pH-value.

In a set-up of the afore-mentioned type for implementation of the method described by the present invention—the sample to be measured being in contact with an enzyme reactant—the reactant is attached to the end of an optical fiber and a photodetector with subsequent signal evaluation is provided, which will measure the fluorescent light emitted by the enzyme reactant or its reaction products, or the excitation light reflected. With the use of a beam splitter, part of the excitation light may be transmitted to a reference photodetector, which will help to eliminate fluctuations of the excitation light source. Depending on the type of task or the nature of the enzyme, several test arrangements may be used. It is a common feature of all arrangements, however, that a synthetic enzyme reactant, for example, is provided at the end of an optical fiber, and that the change in spectral properties is monitored by means of an optical fiber.

Suitable photodetectors are photomultipliers, phototransistors and photodiodes. As photodiodes are inexpensive but sensitive in the visual spectral range only, the preferred enzyme reactants used by the invention are those whose decomposition may be observed at wavelengths greater than 450 nm, ideally above 500 nm. The main advantage of an analytic wavelength of more than 460 nm is that cheap light-emitting diodes may be used as light sources.

Suitable light sources are electric bulbs, gas discharge lamps, LEDs and lasers. Instead of a beam splitter, a dichroic mirror may be used for better separation of the scattered or reflected excitation light and the fluorescent light. Preferably, the optical fiber is a single fiber, but it may also be configured as a multi-fiber bundle.

The separation of fluorescent light and reflected excitation light may also be achieved by means of filters, of course.

In one of the set-ups described by the invention the enzyme reactant is provided at the end of the optical fiber in chemically or physically immobilized form. In this instance the reactant is directly immobilized on the polished exit surface of the optical fiber. The enzyme reactant also may be immobilized along the circumference of the fiber core, however, after the sheathing has been removed from the end of the optical fiber. In this case the decrease in light intensity, or the fluorescent light, is caused by the so-called evanescent light wave, since in case of total reflection at the boundary surface of the optical fiber the electromagnetic wave will penetrate into the enzyme reactant, i.e., the medium of lesser optical density, to a depth of several nanometers. The excitation light may be absorbed there, or may induce fluorescence, provided there is a dye within the penetration depth of the evanescent wave. Reflected or emitted light is retransmitted through the optical fiber and subsequently measured.

Enzyme reactants may be immobilized in various ways. For example, the reactant derived from cumarin, whose structure is as follows,

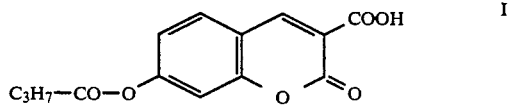

and which is suitable for determining butyrylic choline esterase, was immobilized at the end of an optical fiber as is described below.

The bare end of an optical quartz fiber of 200 μm thickness was finely polished and activated with a 20% aqueous solution of sulphuric acid in order to remove ionic surface contaminations and to improve chemical reactivity of the surface. Subsequently, the glass surface was reacted with the glass derivatisation reagent aminopropyl triethoxylane in a known manner. This reaction is essentially achieved by immersing the active surface of the glass into a 10% solution of the silane in toluene and heating it to 100° C. After 2 hours of heating the glass is rinsed with acetone and dried at 120° C. In this way an optical fiber is obtained with free amine groups at its end.

By means of conventional chemical methods enzyme reactants may be linked to these amine groups. The above reactant I was immobilized by means of the peptide coupling reagent ethyl-N'-(3-dimethylaminopropyl)-carbodiimide hydrochloride.

As an alternative, the reactant may be converted into the respective carboxylic acid chloride and subsequently be reacted with the amine groups of the glass surface.

If the ends of the optical fiber obtained in this way are treated with a solution containing the butyrylic choline esterase enzyme, a marked increase in light absorption at an analytical wavelength of 410–430 nm may be observed within a short time, as well as an increase in fluorescence intensity at 460–470 nm.

In analogy to this example reactants derived from the same basic molecule may be immobilized, which are typically used with sulphatases, amylases, and proteases of structures II, III, IV, below,

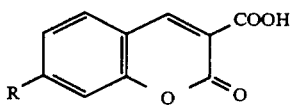

|     |                    |
| --- | ------------------ |
| II  | R= —OSO$_3^-$ Na$^+$ |
| III | R= —O-amylose      |
| IV  | R= amino acid(s)-NH— |

In all instances the enzyme activity of the sample will lead to an increase of absorption at 420 nm, and of fluorescence at 460 nm.

The reactant for use with the lipase enzyme of structure V as below,

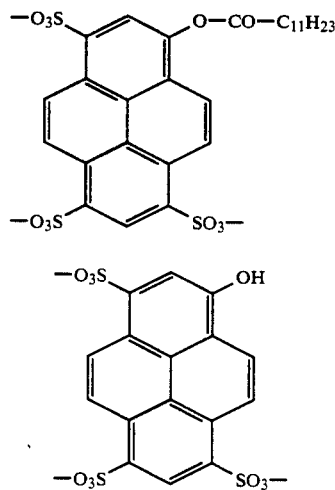

V

VI which is derived from 1-hydroxypyrene-3,6,8-trisulphonate, marked VI in the above drawing, is an example of a synthetic enzyme reactant that may be immobilized electrostatically. Immobilization is due here to the interaction between the negatively charged sulphonate groups of the reactant and the positively charged surface ammonium groups of the anion exchanger used as a carrier material.

Another variant of the invention provides that the enzyme reactant be immobilized on a thin carrier film which is attached to the end of the optical fiber. Following is a description of a typical preparation of a membrane using an electrostatically immobilised enzyme reactant.

An anion exchange membrane is dipped into a solution of 1 g 1-hydroxypyrene-3,6,8-trisulphonate VI in 50 ml methanol. After 2 minutes approx. the membrane whose colour is yellow and whose fluorescence is green, is removed from the bath and rinsed with 0.06 molar phosphate buffer (pH7) before rinsing it with water. After drying, the membrane is put into a solution of 100 mg lauric acid anhydride in dioxan, and VI—which is bonded to the surface of the membrane—will be converted into V. The solution of the lauric acid anhydride is made by dissolving 0.1 g lauric acid in 1 ml dioxan, and adding 0.1 g N,N'-dicyclohexyl carbodiimide, filtering off precipitation. After 2 hours the membrane may be removed from the solution and rinsed with dry acetone. The shade of its fluorescence will now be a blue-purple, its yellow colour will have disappeared.

If this membrane is attached to the end of an optical fiber and treated with a solution of the lipase enzyme, the reactant will be converted by the enzyme into a hydrolytic product of a yellow colour and vivid green fluorescence. The increase of absorption at 460 nm, and of green fluorescence at 520–535 nm, is monitored by the optical fiber. It is a direct measure of the enzyme activity prevalent in the sample. Decomposition of this reactant is effected not only by the lipase enzyme but also by the influence of serum albumin. Since the activity of the latter often is considerably higher, the sensor may also be used for determination of the albumin content in human serum, e.g., in blood.

The latter method may also be used for preparation of other immobilized enzyme reactants for hydrolases. It is not only an alternative method of preparing enzyme-sensitive films, but may also be used for regeneration of sensors that have already been exhausted.

Decomposition of the immobilized enzyme reactants effected by various hydrolases will take place on a solid surface, i.e., the reactant carrier. In chemically immobilized reactants such decomposition processes often take much longer than in solutions where the reactants are under attack of the enzymes from all sides. The slower the rate of hydrolysis, the stronger will be the disturbing influence due to non-enzymatic hydrolysis of the reactants which will always take place on a small scale.

The rate of enzyme hydrolysis of immobilized synthetic reactants may be considerably increased if long-chain spacer groups are provided between the surface of the optical fiber, or rather that of the carrier film, and the enzyme reactant, as has been proposed by the invention.

Suitable spacer groups are long-chain diamines for instance, such as hexamethylene diamine. Spacer groups may also be introduced together with the silylation reagent, for instance by means of long-chain amines.

In order to prevent strongly coloured sample substances, such as blood, from affecting the optical system, the end of the optical fiber may be covered by a protective cap which will keep out large coloured particles, e.g., erythrocytes. On the other hand, enzymes will be able to penetrate the cap. The ideal material for protein-permeable caps is cellulose.

Instead of immobilizing the enzyme reactants directly at the end of an optical fiber, another variant of the invention provides that the end of the optical fiber be enclosed by an enzyme-permeable membrane serving as a reaction chamber, which contains the enzyme reactant and is impermeable to cellular components of the sample. Such a reaction chamber should be permeable to the enzyme to be tested, but it should not permit the enzyme reactant to leave by diffusion.

According to the invention the enzyme reactant may be prevented from diffusing out of the membrane by bonding it to a water-soluble or water-swelling polymer, e.g., by chemical immobilization. Water-soluble or swelling polymers which may be used as carriers for the enzyme reactants in the reaction chamber, include dextran, agarose, polyethyleneimine, polyacrylamide and polyalcohols. The respective polymer carrier should be chosen such that its molecules are large enough to prevent escape through the protective cap. The immobilized reactant is split by enzymatic hydrolysis, thus suffering a change in its spectral properties. This change is monitored via the optical fiber and serves as a measure of enzyme activity. Since the dye release during this process can diffuse out of the cellulose membrane to a certain extent, it is absobutely necessary that the enzyme reaction should take considerably less time than the diffusion process.

In the set-up discussed in the above paragraph only enzyme reactants can be used whose spectral properties are noticeably changed by the enzyme reaction. This is due to the fact that the optical fiber will carry the signals of both the enzyme reactant and its products of decomposition. For this reason the proposal is put forward in a further development of the invention that the enzyme reactant be immobilized on the inner surface of a preferably cylindrical reaction chamber positioned at the end of the optical fiber, the chamber being furnished with an enzyme-permeable membrane on the side facing the sample, which membrane should be impermeable to cellular sample components, and that the reaction products generated by enzyme reaction be diffused into the reaction chamber. Due to the spatial separation of the reactant and its products of decomposition, generation of the latter may be specifically observed.

Optical separation is achieved in a simple manner, by choosing the diameter and length of the reaction cylinder for a given exit angle α of the excitation light such that direct excitation of the enzyme reactant is avoided. The cylinder wall and the reactant applied on its surface will now be located outside the numerical aperture of the optical fiber defined by the exit angle α, and the reactant will produce no signal in the optical fiber as long as there is no enzyme reaction.

As soon as the enzyme to be measured enters the reaction chamber an enzyme reaction will take place which is accompanied by the release of a dye. The dye will disperse in the reaction chamber, and its colour or fluorescence will be detected by the optical fiber. The increase in colour or fluorescence intensity is used as a measure of catalytic enzyme activity.

The above set-up has a number of elementary advantages.

(a) Because of their spatial separation there will be no spectral overlap between enzyme reactant and decomposition product, which will eliminate high blank values.

(b) In addition to synthetic enzyme reactants, natural reactants may be used which are marked with a dye.

The following examples will illustrate the wide range of applications of the set-up described by the invention; in most cases immobilization is achieved by chemically bonding polymer carrier, spacer groups and the dyes proper.

(1) Immobilization of 7-hydroxycumarin-3-carboxylic acid via a spacer group (adipic acid) on a cellulose membrane or on the surface of another polymer carrying OH groups, will lead to a surface structure as below.

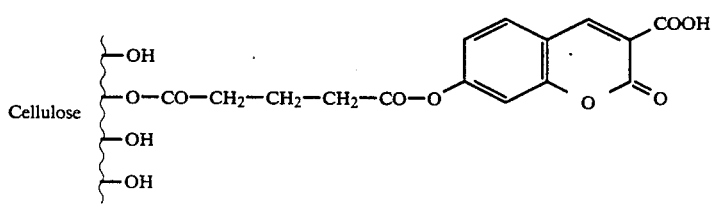

The splitting of the CO—O bond effected by an enzyme from a group of carboxyl esterases will result in the release of a dye which will diffuse into the field of vision of the optical fiber and may then be measured.

(2) Immobilization of 3-cyano-7-hydroxycumarin on OH-containing polymers via a $CH_2$—$CH_2$—$CH_2$—$CH_2$ spacer group will lead to a structural element of the following chemical formula:

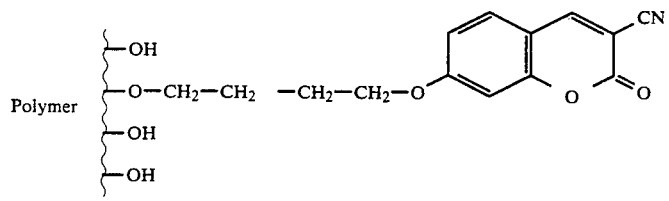

The immobilized dye resulting from this process is a synthetic reactant for dealkylases. The latter will split the ether groups, thereby releasing the fluorescent dye 7-hydroxycumarin-3-carboxylic acid, which may be detected by the optical fiber.

(3) Following is the structural element of a protease reactant immobilized on a glass surface:

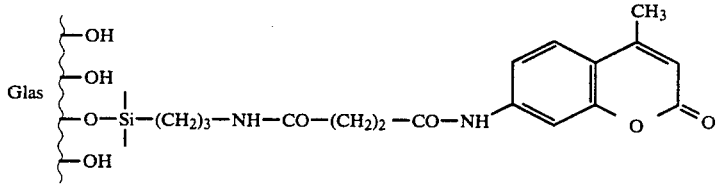

Not only synthetic reactants, but also natural reactants marked with a dye may be immobilized on the surface of the reaction chamber, for instance proteins. For example, egg albumin lysozyme can be immobilized on the surface of the wall and then marked with a fluorescent dye, e.g. fluoresceinisothiocyanate. Upon contact with the enzyme trypsin this reactant will decompose. Fluorescein and fluorescein-marked fragments of the lysozyme will diffuse into the field of vision of the optical fiber where they can be measured by fluorometric methods.

Immobilized proteins are easy to prepare but may also be obtained ready-made. Besides, saccharides, i.e., sugar-like bonds, are commercially available in immobilized form, e.g., immobilized N-acetylglucosamine, lactose, melibiose, N-acetylgalactosamine, fucose, mannose, cellobiose, galactose and glucose. These substances may be applied to the wall of the reaction chamber and marked with a dye. Suitable dyes are fluorescein-isothiocyanate, dansyl chloride, fluorescamine, naphthylisocyanate and europium chelates. The marked molecules will be released upon enzyme reaction and will then diffuse into the reaction chamber and be detected by the optical fiber.

The material enclosing the reaction chamber may itself be the reactant. For this purpose amylose may be used, for instance, from the group of polyglucosides, which must be marked with a fluorescent dye on the inner surface of the wall of the reaction chamber. Other substances which may be used as both reactants and wall-materials, include polypeptides and fatty acid esters. It goes without saying that water-insoluble substances may be used only.

The advantage of using dyed natural enzyme reactants is that the high specificity of enzymes for natural reactants may be put to use in this way. In combination with fluorometry the object of finding both a sensitive and specific method of determination has been achieved.

Many enzymes occur in more than one form, i.e., they may form sub-groups. A typical example are the phosphatases. There are phosphatases which have their activity maximum in alkaline solution, i.e., alkaline phosphatases, and others with their activity maximum in axid solution, i.e. acid phosphatases. Acid phosphatase, which is of clinical importance, can no longer be determined at pH 7.4, for instance, without including—at least partly—the activity of the alkaline phosphatases.

This problem can be avoided by using a set-up including two enzyme-sensitive fiber-optical catheters. These catheters must differ in that the two enzyme reactants on their respective catheter ends must have different enzyme affinities and must also differ in their maximum reaction rates. The affinity of an enzyme for a reactant is given by the Michaelis-Menten constant, maximum velocity is given by a quantity indicating the maximum reaction rate.

DESCRIPTION OF THE DRAWINGS

The following is a more detailed description of preferred embodiments of the invention, by way of example, reference being made to the accompanying drawings, in which.

DETAILED DESCRIPTION OF THE PREFERRED EMBODIMENTS

Figure 1:
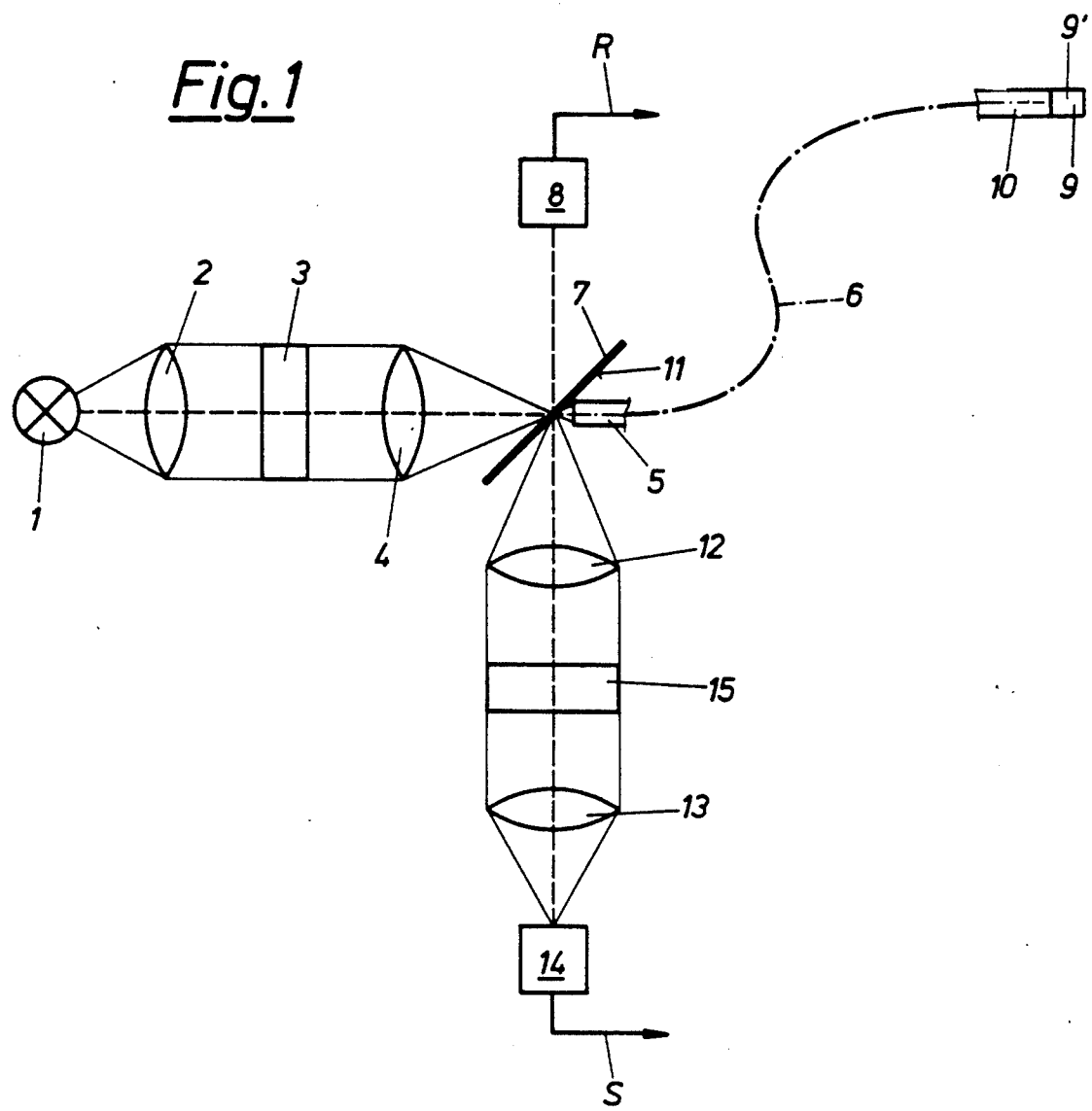
FIG. 1 is a schematic view of a set-up as described by the invention.

In FIG. 1 the light issuing from the light source 1 is collected with a collimating lens 2 and coupled into the entrance end 5 of an optical fiber 6 by a focusing lens 4 after having passed a filter 3. By means of this filter 3 the wavelength of the light is adjusted to the absorption maximum of the dye released upon enzyme hydrolysis. Part of the light is directed onto a reference photodetector 8 by means of a beam splitter 7. The reference detector 8 is used to eliminate fluctuations in the intensity of the light source 1.

Via the optical fiber 6 the light is transmitted to the enzyme reactant 9 which may be synthetic, for example, and which is immobilized on the exit end 10 of the optical fiber 6. If the enzyme reactant 9 is split by a suitable enzyme, the incident light is increasingly absorbed and thus weakened by the formation of coloured reaction products 9'. If the respective dye is capable of fluorescence, a continuous increase in fluorescence intensity may be observed, on the other hand.

Both reflected and fluorescent light are retransmitted through the same optical fiber 6 and directed onto a photo-detector 14 via the half mirror-coated surface 11 of the beam splitter 7 by means of lenses 12, 13. When measuring fluorescence another optical filter 15 is inserted between the beam splitter 7, or rather the lens 12, and the detector 14, which filter 15 is impervious to reflected exitation light, thus permitting selective detection of the fluorescent light. The signal S measured at the photo-detector 14, and the reference signal R measured at the reference photodetector 8, is amplified and fed to a display/evaluation unit, not shown in this drawing.

Figure 2:
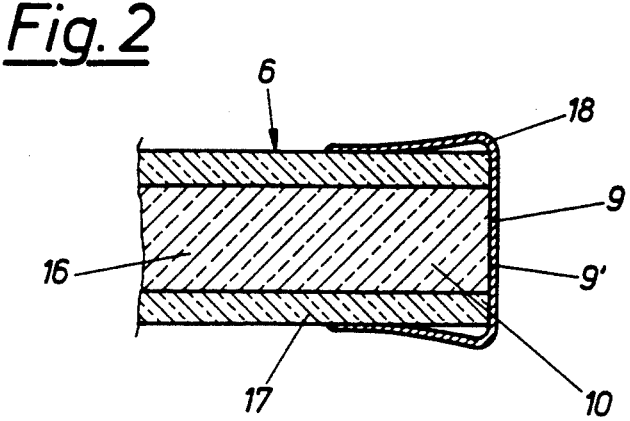
FIGS. 2-5 present variants of a detail from FIG. 1.

FIG. 2 is an enlarged view of the end 10 of the optical fiber 6 whose core 16 and sheathing 17 have different refraction coefficients. The reactant 9 is immobilized on a thin carrier film 18, for instance made of cellulose, ion exchange membrane or polyacrylamide, which will then be attached to the exit end 10 of the optical fiber 6.

Figure 3:
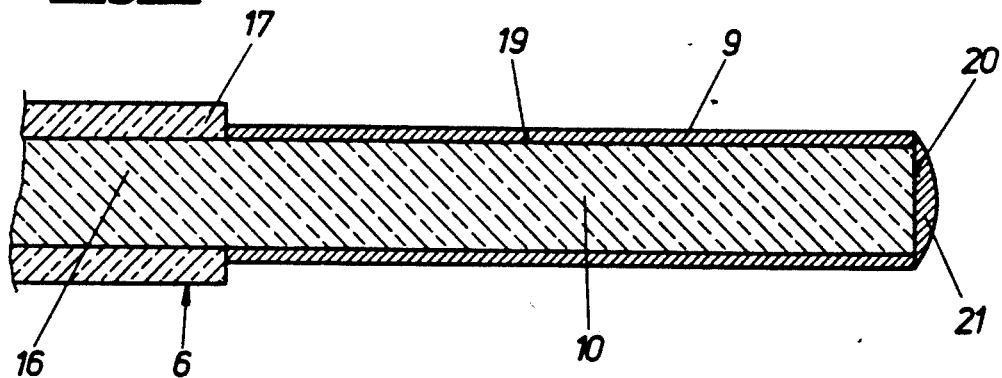

As shown in FIG. 3, the enzyme reactant 9 may also be applied on the outer surface 19 of the cylindrical core 16 of an optical fiber 6; in this instance the sheathing 17 is stripped off the end of the optical fiber 6, which may be provided with a light-reflecting cap 21 over its circular exit surface 20.

Figure 4:
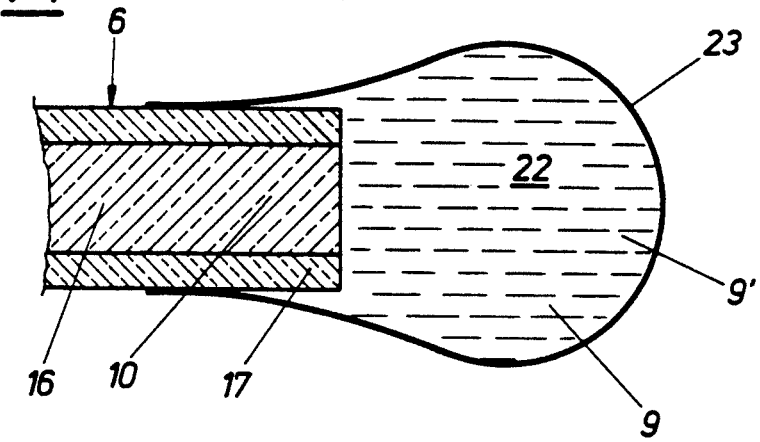

FIG. 4 again is a schematic view of the end 10 of an optical fiber 6 which carries a bubble-shaped reaction chamber 22 bounded by a protein-permeable membrane 23 made of cellulose, for example. The reaction chamber 22 contains the enzyme reactant 9 which consists of relatively small molecules and would therefore diffuse out through the wall of the membrane. In order to prevent such diffusion the enzyme reactant 9 is immobilized on a water-soluble polymer with larger-size molecules. Suitable carriers for the enzyme reactants in the reaction chamber 22 are water-soluble or swelling polymers.

Figure 5:
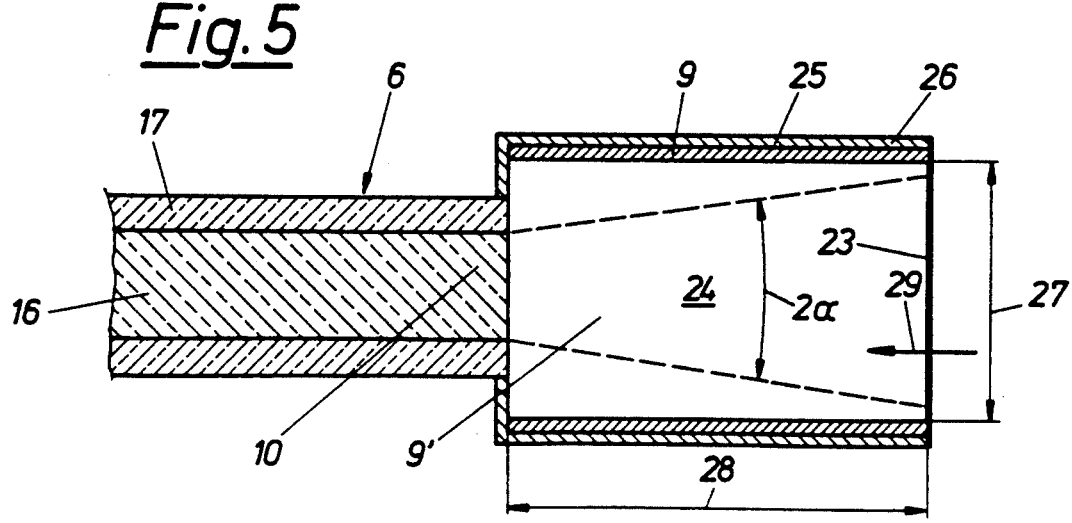

With the set-up present in FIG. 5 the reaction products 9' can be spatially separated from the original enzyme reactant 9. In this set-up there is a cylindrical reaction space 24 at the end 10 of an optical fiber 6, whose side facing the sample is covered by an enzyme-permeable membrane 23, for instance made of cellulose or a porous polycarbonate. The inside of the wall 25 of the cylinder 26 containing the reaction space 24 is lined with the coloured or fluorescent enzyme reactant 9. Unlike in the set-ups discussed before, the reactant 9 is not homogeneously dispersed throughout the reaction space, but is held on the inside of wall 25 of the cylinder 26 by chemical, electrostatic or physical immobilization.

As soon as the enzyme to be determined enters the reaction space 24 through the membrane 23 in the direction indicated by arrow 29, enzyme reaction will set in, releasing reaction products 9'. The reaction products 9' may move freely within the reaction space 24 and will also diffuse in the region defined by the exit angle α of the excitation light. The diameter 27 and length 28 of the cylinder 26 containing the reaction space, should be chosen such that the excitation light leaving the optical fiber will not fall upon the wall of the cylinder or the enzyme reactant 9 immobilized thereon.

I claim:

1. A method for the optical determination of the catalytic enzyme activity of a sample containing an enzyme, comprising the steps of:
    a) immobilizing an enzyme substrate at one end of an optical fiber,
    b) bringing said enzyme substrate into contact with said sample to effect enzyme reaction and the formation of an immobilized reaction product having different spectral properties than said enzyme substrate,
    c) detecting changes in at least one of said spectral properties due to said enzyme reaction, and
    d) determining a value of catalytic enzyme activity from said changes in spectral properties detected in step c).

2. A method according to claim 1, wherein said change in at least one of said spectral properties is a change in absorption.

3. A method according to claim 1, wherein said enzyme substrate is synthetic.

4. A method according to claim 1, wherein said change in at least one of said spectral properties is a spectral change in fluorescence radiation.

5. A method according to claim 4, wherein said change in fluorescence radiation is a change in fluorescence intensity.

6. A method according to claim 4, wherein said change in fluorescence radiation is a shifting of a fluorescence maximum.

7. A method according to claim 1, including the step of determining the pH value of said sample, said pH value being used to correct said value of catalytic enzyme activity determined in step d).

8. An arrangement for the optical determination of the catalytic enzyme activity of a sample containing an enzyme, comprising an optical fiber having a first end and a second end; an enzyme substrate immobilized on said first end of said optical fiber, said enzyme substrate being converted to an immobilized reaction product having different spectral properties than said enzyme substrate upon reaction with said enzyme; and a photodetector with signal evaluation means attached to said second end of said optical fiber, said photodetector measuring the fluorescent light emitted by an immobilized reaction product produced when said enzyme substrate is placed in contact with a sample containing an enzyme.

9. An arrangement according to claim 8, wherein said enzyme substrate is provided at said first end of said optical fiber in chemically or physically immobilized form.

10. An arrangement according to claim 9, wherein long-chain spacer groups are provided between the surface of said optical fiber and said enzyme substrate.

11. An arrangement according to claim 8, wherein said enzyme substrate is immobilized on a thin carrier film which is attached to said first end of said optical fiber.

12. An arrangement according to claim 11, wherein long-chain spacer groups are provided between said carrier film and said enzyme substrated.

13. An arrangement according to claim 8, wherein said first end of said optical fiber is enclosed by an enzyme-permeable membrane forming a reaction chamber, which contains said enzyme substrate, said enzyme-permeable membrane being impermeable to cellular components of said sample.

14. An arrangement according to claim 13, wherein said enzyme substrate is bonded to a water-soluble polymer.

15. An arrangement according to claim 13, wherein said enzyme substrate is bonded to a water-swelling polymer.

16. A method for optically determining the catalytic enzyme activity of a sample containing an enzyme, said method comprising the steps of:
    (a) immobilizing an enzyme substrate which has first characteristic spectral properties at one end of an optical fiber,
    (b) passing excitation light through said optical fiber so as to contact said enzyme substrate and cause said enzyme substrate to irradiate said first characteristic spectral properties into said optical fiber,
    (c) detecting a value of one of said spectral properties,
    (d) placing said one end of said optical fiber in contact with said sample such that the enzyme of said sample and said enzyme substrate react to form a reaction product which has second characteristic spectral properties,
    (e) detecting a value of one of said second characteristic spectral properties via said optical fiber, and
    (f) comparing said value detected in step (c) with said value detected in step (e) to determine the catalytic enzyme activity of said sample.

* * * * *